(12) United States Patent
Hikmawan et al.

(10) Patent No.: US 11,782,044 B2
(45) Date of Patent: Oct. 10, 2023

(54) WATER QUALITY SAMPLER

(71) Applicant: Saudi Arabian Oil Company, Dhahran (SA)

(72) Inventors: Tyas Ikhsan Hikmawan, Khobar (SA); Perdana Karim Prihartato, Dhahran (SA); Maryam Saber Qashqari, Dhahran (SA); Ali Mothana Qasem, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/508,274

(22) Filed: Oct. 22, 2021

(65) Prior Publication Data

US 2023/0125771 A1    Apr. 27, 2023

(51) Int. Cl.
*G01N 33/18* (2006.01)
*G01N 1/10* (2006.01)
(Continued)

(52) U.S. Cl.
CPC ........... *G01N 33/1833* (2013.01); *G01N 1/10* (2013.01); *G01N 2001/1031* (2013.01)

(58) Field of Classification Search
CPC ................ G01N 33/1833; G01N 1/10; G01N 2001/1031; G01N 2001/1093; G01N 2001/4088; G01N 1/12; G01N 1/16; G01N 1/4005; G01N 33/18; G01N 33/1826; B65D 21/0209; B65D 21/0213; B65D 21/0216; B65D 21/0233; B65D 21/0234; B65D 21/04; B65D 21/041; B65D 21/048; B65D 21/02
See application file for complete search history.

(56) References Cited

U.S. PATENT DOCUMENTS 3,424,334 A * 1/1969 Goltz ................. B65D 21/0202
220/23.6

FOREIGN PATENT DOCUMENTS

| CA | 2820177 A1 * | 1/2014 | .............. B01L 3/502 |
| GB | 1586749 A * | 3/1981 | .............. G01N 30/00 |
| GB | 2467520 A * | 8/2010 | ........... G01N 33/186 |

OTHER PUBLICATIONS

Fones et al.; "Evaluation of DGT as a long-term water quality monitoring tool in natural waters; uranium as a case study"; 2014; vol. 16, No. 3; pp. 393-403 (Year: 2014).*

(Continued)

*Primary Examiner* — Herbert K Roberts
*Assistant Examiner* — Anthony W Megna Fuentes
(74) *Attorney, Agent, or Firm* — DINSMORE & SHOHL LLP

(57) ABSTRACT

A water quality sampler includes a membrane receptacle and at least 7 sample membranes. The membrane receptacle comprises at least 7 membrane cavities disposed on a top surface of the membrane receptacle. Each membrane cavity is configured to hold a sample membrane and the sample membranes are each removably positioned within the membrane cavities and extend at least 1 cm out from the top surface of the membrane receptacle. A bottom of the membrane receptacle comprises a protruding lip that traces a bottom edge of the membrane receptacle in a downward direction, where the protruding lip encompasses a stacking chamber capable of receiving a top end of a second water quality sampler to allow stacking of multiple water quality samplers.

16 Claims, 1 Drawing Sheet

(51) Int. Cl.
    *G01N 1/12*        (2006.01)
    *G01N 1/40*        (2006.01)
    *G01N 1/16*        (2006.01)

(56)            References Cited

OTHER PUBLICATIONS

Monitool New Tools for Water Quality Monitoring, by Interreg Atlantic Area European Regional Development Fund, European Union, https://www.monitoolproject.eu/multimedia/photos/dgt, accessed Jan. 22, 2021.

* cited by examiner

WATER QUALITY SAMPLER

BACKGROUND

The present disclosure relates to water quality samplers. More specifically, it relates to water quality samplers capable of stacking to allow for more effective sampling.

BRIEF SUMMARY

Passive sampling is an environmental monitoring technique that has a key role in water quality monitoring by measuring the concentration of a wide range of pollutants including organic components, hydrocarbons and trace metals. This technique provides accumulative concentration of chemicals over time. Passive sampler could be beneficial for monitoring the level of water quality during offshore operation such as trenching and dredging activities. This technique can improve the efficiency of compliance monitoring. Moreover, it can be used to assess the quality of discharges from the company's off-shore and coastal facilities. Conventional sampling methods are directed towards testing for one contaminant or chemical target at a time. The present disclosure is directed to a water quality sampler designed to accommodate multiple types of passive sampler membranes to detect various targets at once.

According to the subject matter of the present disclosure a water quality sampler includes a membrane receptacle and at least 7 sample membranes. The membrane receptacle comprises at least 7 membrane cavities disposed on a top surface of the membrane receptacle, wherein each membrane cavity is configured to hold a sample membrane and the sample membranes are each removably positioned within the membrane cavities and extend at least 1 cm out from the top surface of the membrane receptacle. A bottom of the membrane receptacle includes a protruding lip that traces a bottom edge of the membrane receptacle in a downward direction, where the protruding lip encompasses a stacking chamber capable of receiving a top end of a second water quality sampler to allow stacking of multiple water quality samplers.

In accordance with another embodiment of the present disclosure, a water quality sampler includes a membrane receptacle comprising high-density polyethylene and 10 pollutant sampling membranes comprising hydrocarbon sampling membranes, organic sampling membranes, metal sampling membranes, or combinations thereof. The membrane receptacle includes 8 membrane cavities disposed on a top surface of the membrane receptacle. Each membrane cavity is configured to hold a sample membrane and the sample membranes are each removably positioned within the membrane cavities and extend at least 1 cm out from the top surface of the membrane receptacle. A bottom of the membrane receptacle comprises a protruding lip that traces a bottom edge of the membrane receptacle in a downward direction. The protruding lip encompasses a stacking chamber capable of receiving a top end of a second water quality sampler to allow stacking of multiple water quality samplers, 2 membrane cavities are disposed on the bottom of the membrane receptacle, and a sidewall of the membrane receptacle comprises an attachment socket configured to connect to a hook, a rope, a weight, or combinations thereof.

In accordance with another embodiment of the present disclosure, a method of determining water quality includes lowering a water quality sampler into a sea, where the water quality sampler includes a membrane receptacle and at least 7 sample membranes. The at least 7 membrane cavities are disposed on a top surface of the membrane receptacle. Each membrane cavity holds a sample membrane, the sample membranes are each removably positioned within the membrane cavities and extend at least 1 cm out from the top surface of the membrane receptacle. A bottom of the membrane receptacle includes a protruding lip that traces a bottom edge of the membrane receptacle in a downward direction, where the protruding lip encompasses a stacking chamber, and a sidewall of the membrane receptacle comprises an attachment socket where the attachment socket is connected to a hook, a rope, a weight, or combinations thereof. The method further includes allowing water to pass through the at least 7 sample membranes; raising the water quality sampler out of the sea and analyzing the at least 7 sample membranes to determine water quality.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

The present disclosure is directed to a water quality sampler designed to accommodate different types of passive sampler membranes to detect various targets at once. It can be stacked in order to increase the number of samplers. The water quality sampler of the present disclosure additionally includes high-density polyethylene (HDPE) are resistant to high temperature and high saline water, such as the water in the Arabian Gulf.

Figure 1:
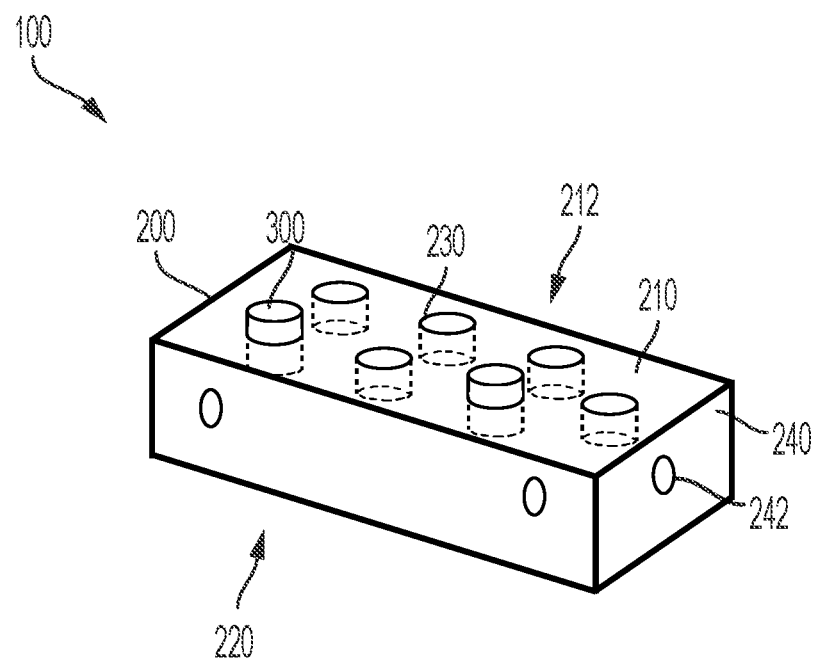
FIG. 1 illustrates a water quality sampler, according to one or more embodiments described in this disclosure.
Figure 2:
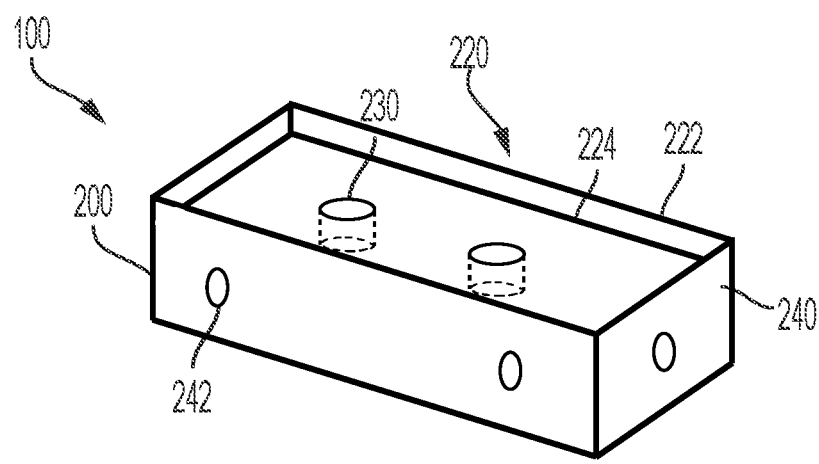
FIG. 2 illustrates a water quality sampler, according to one or more embodiments described in this disclosure.

Referring to FIGS. 1 and 2, a water quality sampler 100 is shown. The water quality sampler 100 includes a membrane receptacle 200 and at least 7 sample membranes 300. The membrane receptacle includes a top surface 210 and a bottom 220. The bottom 220 of the membrane receptacle 200 includes a protruding lip 222 that traces a bottom edge 224 of the membrane receptacle in a downward direction. The protruding lip 222 encompasses a stacking chamber 230 capable of receiving a top end 212 of a second water quality sampler 100 to allow stacking of multiple water quality samplers 100. Specifically, the protruding lip 222 may be capable of receiving a top end 212 of the membrane receptacle 200 within the stacking chamber 230, thereby allowing stacking of multiple water quality samplers 100.

The membrane receptacle 200 may further include a sidewall 240. The sidewall 240 may be rectangular (as shown in FIGS. 1 and 2), or rounded to form a cylinder or a semi-cylinder (not shown). In embodiments, the sidewall 240 may fully or at least partially surround the membrane receptacle 200 and/or the stacking chamber 230. As clearly illustrated in both FIGS. 1 and 2, the sidewall 240 may extend continuously from the top surface 210 to the bottom 220 of the membrane receptacle 200, such that the membrane receptacle is monolithic.

As stated previously, the water quality sampler 100 includes at least 7 sample membranes 300. In embodiments, the sample membranes 300 may include pollutant sampling membranes. The pollutant sampling membranes may include hydrocarbon sampling membranes, organic sampling membranes, metal sampling membranes, or combinations thereof.

The membrane receptacle 200 further includes at least 7 membrane cavities 230 disposed on the top surface 210 of the membrane receptacle 200. Each membrane cavity 230 is configured to hold a sample membrane 300. The sample membranes 300 are each removably positioned within the membrane cavities 230. The sample membranes 300 extend at least 1 cm out from the top surface 210 of the membrane receptacle 200. In embodiments, the sample membranes 300 may extend from 1 to 5 cm, from 1 to 4 cm, from 1 to 3 cm, from 1 to 2 cm, from 2 to 5 cm, from 2 to 4 cm, from 2 to 3 cm, from 3 to 5 cm, from 3 to 4 cm, or from 4 to 5 cm out from the top surface 210 of the membrane receptacle 200.

In embodiments, the bottom 220 of the membrane receptacle 200 may include a membrane cavity 230. As stated previously, the membrane receptacle 200 includes at least 7 membrane cavities on the top surface 210, which means the top surface 210 may have 7 membrane cavities, 8 membrane cavities, 9 membrane cavities, 10 membrane cavities As a non-limiting example, there may be 8 membrane cavities 230 disposed on the top surface 210 of the membrane receptacle 200 and 2 membrane cavities 230 disposed on the bottom 220 of the membrane receptacle 200. In embodiments, the bottom of the membrane receptacle 200 may include 1 membrane cavity 230, 2 membrane cavities 230, 3 membrane cavities 230, 4 membrane cavities 230, or 5 membrane cavities 230.

The membrane receptacle 200 may further include an attachment socket 242 disposed on the sidewall 240 of the membrane receptacle 200. The attachment socket 242 may be configured to connect to a hook, a rope, a weight, of combinations thereof. The attachment socket 242 may be any attachment socket known in the art to connect a hook, a rope, or a weight to the membrane receptacle 200.

The water quality sampler 100 includes may include thermoplastic polymer. In embodiments, the water quality sampler 100 includes high-density polyethylene (HDPE).

Methods of using the water quality sampler 100 are also described. The methods include lowering the water quality sampler 200 into a body of water. The water quality sampler 200 may be any of the embodiments described previously. The body of water may be a sea, an ocean, a lake, a pool, a river, or any other body of water. The methods further include allowing water to pass through the at least 7 sample membranes 300, raising the water quality sampler 100 out of the body of water, and analyzing the at least 7 sample membranes 300 to determine water quality. Lastly, the methods may further include producing hydrocarbons from a subsea well before lowering the water quality sampler into the sea.

It is noted that recitations herein of a component of the present disclosure being "configured" in a particular way, to embody a particular property, or to function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is possible that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A water quality sampler comprising a membrane receptacle and at least 7 sample membranes, wherein:
   the membrane receptacle has a top surface, a bottom, and a sidewall extending continuously from the top surface to the bottom, such that the membrane receptacle is monolithic;
   the membrane receptacle comprises at least 7 membrane cavities disposed on the top surface of the membrane receptacle, wherein each membrane cavity is configured to hold a sample membrane;
   the sample membranes are each removably positioned within the membrane cavities and extend at least 1 cm out from the top surface of the membrane receptacle; and
   the bottom of the membrane receptacle comprises a protruding lip that traces a bottom edge of the membrane receptacle in a downward direction, where the protruding lip encompasses a stacking chamber capable of receiving a top end of a second water quality sampler to allow stacking of multiple water quality samplers.

2. The water quality sampler of claim 1, wherein the water quality sampler comprises high-density polyethylene.

3. The water quality sampler of claim 1, wherein the bottom of the membrane receptacle comprises a membrane cavity.

4. The water quality sampler of claim 1, wherein the sidewall of the membrane receptacle comprises an attachment socket.

5. The water quality sampler of claim 4, wherein the attachment socket is configured to connect to a hook, a rope, a weight, or combinations thereof.

6. The water quality sampler of claim 1, wherein the sample membranes comprise pollutant sampling membranes.

7. The water quality sampler of claim 6, wherein the pollutant sampling membranes comprise hydrocarbon sampling membranes, organic sampling membranes, metal sampling membranes, or combinations thereof.

8. The water quality sampler of claim 1, wherein the water quality sampler comprises 8 membrane cavities disposed on the top surface of the membrane receptacle and 2 membrane cavities disposed on the bottom of the membrane receptacle.

9. A water quality sampler comprising a membrane receptacle comprising high-density polyethylene and 10 pollutant sampling membranes comprising hydrocarbon sampling membranes, organic sampling membranes, metal sampling membranes, or combinations thereof, wherein: the membrane receptacle has a top surface, a bottom, and a sidewall extending continuously from the top surface to the bottom, such that the membrane receptacle is monolithic; the membrane receptacle comprises 8 membrane cavities disposed on the top surface of the membrane receptacle, wherein each membrane cavity is configured to hold a sample membrane; the sample membranes are each removably positioned within the membrane cavities and extend at least 1 cm out from the top surface of the membrane receptacle; the bottom of the membrane receptacle comprises a protruding lip that traces a bottom edge of the membrane receptacle in a downward direction, where the protruding lip encompasses a stacking chamber capable of receiving a top end of a second water quality sampler to allow stacking of multiple water quality samplers; 2 membrane cavities are disposed on the bottom of the membrane receptacle; and the sidewall of the membrane receptacle comprises an attachment socket configured to connect to a hook, a rope, a weight, or combinations thereof.

10. A method of determining water quality comprising: lowering a water quality sampler into a sea, where the water quality sampler comprises a membrane receptacle and at least 7 sample membranes, wherein: the membrane receptacle has a top surface, a bottom, and a sidewall extending continuously from the top surface to the bottom, such that the membrane receptacle is monolithic; the membrane receptacle comprises at least 7 membrane cavities disposed on the top surface of the membrane receptacle, wherein each membrane cavity holds a sample membrane, the sample membranes are each removably positioned within the membrane cavities and extend at least 1 cm out from the top surface of the membrane receptacle, and the bottom of the membrane receptacle comprises a protruding lip that traces a bottom edge of the membrane receptacle in a downward direction, where the protruding lip encompasses a stacking chamber, and the sidewall of the membrane receptacle comprises an attachment socket where the attachment socket is connected to a hook, a rope, a weight, or combinations thereof; allowing water to pass through the at least 7 sample membranes; raising the water quality sampler out of the sea; and analyzing the at least 7 sample membranes to determine water quality.

11. The method of claim 10, further comprising producing hydrocarbons from a subsea well before lowering the water quality sampler into the sea.

12. The method of claim 10, wherein the water quality sampler comprises high-density polyethylene.

13. The method of claim 10, wherein the bottom of the membrane receptacle comprises a membrane cavity.

14. The method of claim 10, wherein the sample membranes comprise pollutant sampling membranes.

15. The method of claim 14, wherein the pollutant sampling membranes comprise hydrocarbon sampling membranes, organic sampling membranes, metal sampling membranes, or combinations thereof.

16. The method of claim 10, wherein the water quality sampler comprises 8 membrane cavities disposed on the top surface of the membrane receptacle and 2 membrane cavities disposed on the bottom of the membrane receptacle.

* * * * *